US007745400B2

(12) United States Patent
Feinerman et al.

(10) Patent No.: US 7,745,400 B2
(45) Date of Patent: Jun. 29, 2010

(54) PREVENTION AND TREATMENT OF OCULAR SIDE EFFECTS WITH A CYCLOSPORIN

(76) Inventors: Gregg Feinerman, 46 Emerald, Irvine, CA (US) 92614; Neil Barth, 1813 E. Bay Ave., Newport Beach, CA (US) 92661; Rhett M. Schiffman, 1843 Temple Hills Dr., Laguna Beach, CA (US) 92651; Pamela S. Barnett, 64 Hawaii Dr., Aliso Viejo, CA (US) 92656

( * ) Notice: Subject to any disclaimer, the term of this patent is extended or adjusted under 35 U.S.C. 154(b) by 0 days.

(21) Appl. No.: 11/548,631

(22) Filed: Oct. 11, 2006

(65) Prior Publication Data

US 2007/0167358 A1 Jul. 19, 2007

Related U.S. Application Data

(60) Provisional application No. 60/596,709, filed on Oct. 14, 2005, provisional application No. 60/597,431, filed on Nov. 30, 2005, provisional application No. 60/805,577, filed on Jun. 22, 2006.

(51) Int. Cl.
*A61K 38/13* (2006.01)
(52) U.S. Cl. ....................................................... 514/11
(58) Field of Classification Search ........................ None
See application file for complete search history.

(56) References Cited

U.S. PATENT DOCUMENTS

| 4,388,229 A | 6/1983 | Fu |
| 4,388,307 A | 6/1983 | Cavanak |
| 4,649,047 A | 3/1987 | Kaswan |
| 4,814,323 A | 3/1989 | Andrieu et al. |
| 4,839,342 A | 6/1989 | Kaswan |
| 4,996,193 A | 2/1991 | Hewitt et al. |
| 5,047,396 A | 9/1991 | Orban et al. |
| 5,051,402 A | 9/1991 | Kurihara et al. |
| 5,294,604 A | 3/1994 | Nussenblatt |
| 5,296,158 A | 3/1994 | MacGilp et al. |
| 5,342,625 A | 8/1994 | Hauer et al. |
| 5,411,952 A * | 5/1995 | Kaswan ........................ 514/11 |
| 5,474,979 A | 12/1995 | Ding et al. |
| 5,543,393 A | 8/1996 | Kim et al. |
| 5,589,455 A | 12/1996 | Woo |
| 5,614,491 A | 3/1997 | Walch et al. |
| 5,639,724 A | 6/1997 | Cavanak |
| 5,652,212 A | 7/1997 | Cavanak et al. |
| 5,753,166 A | 5/1998 | Dalton et al. |
| 5,759,997 A | 6/1998 | Cavanak |
| 5,766,629 A | 6/1998 | Cho et al. |
| 5,798,333 A | 8/1998 | Sherman |
| 5,827,822 A | 10/1998 | Floc'h et al. |
| 5,827,835 A | 10/1998 | Kabra |
| 5,834,017 A | 11/1998 | Cho et al. |
| 5,891,846 A | 4/1999 | Ishida et al. |
| 5,916,589 A | 6/1999 | Hauer et al. |
| 5,951,971 A | 9/1999 | Kawashima et al. |
| 5,962,014 A | 10/1999 | Hauer et al. |
| 5,962,017 A | 10/1999 | Hauer et al. |
| 5,962,019 A | 10/1999 | Cho et al. |
| 5,977,066 A | 11/1999 | Cavanak |
| 5,977,067 A | 11/1999 | Evers et al. |
| 6,007,840 A | 12/1999 | Hauer et al. |
| 6,024,978 A | 2/2000 | Hauer et al. |
| 6,057,289 A | 5/2000 | Mulye |
| 6,190,691 B1 | 2/2001 | Mak |
| 6,197,335 B1 | 3/2001 | Sherman |
| 6,245,805 B1 | 6/2001 | Broder et al. |
| 6,254,860 B1 * | 7/2001 | Garst ........................ 424/78.04 |
| 6,254,885 B1 | 7/2001 | Cho et al. |
| 6,267,985 B1 | 7/2001 | Chen et al. |
| 6,284,268 B1 | 9/2001 | Mishra et al. |
| 6,294,192 B1 | 9/2001 | Patel et al. |
| 6,306,825 B1 | 10/2001 | Cavanak |
| 6,350,442 B2 | 2/2002 | Garst |
| 6,420,355 B2 | 7/2002 | Richter et al. |
| 6,468,968 B2 | 10/2002 | Cavanak et al. |
| 6,475,519 B1 | 11/2002 | Meinzer et al. |
| 6,486,124 B2 | 11/2002 | Olbrich et al. |
| 6,569,463 B2 | 5/2003 | Patel et al. |
| 6,582,718 B2 | 6/2003 | Kawashima et al. |

(Continued)

FOREIGN PATENT DOCUMENTS

| EP | 0146341 | 12/1984 |
| EP | 0471293 | 2/1992 |
| EP | 0547229 | 6/1992 |
| EP | 956853 | 5/1999 |
| WO | WO00/00179 | 1/2000 |
| WO | WO/08085 | 2/2000 |
| WO | WO01/32142 | 5/2001 |

OTHER PUBLICATIONS

"Questions and Answers About Taxotere® Injection Concentrate", Patient Information Leaflet by Aventis Pharmaceuticals Inc., Rev. May 2004.*
Schmid et al. Update on Ocular Complications of Systemic Cancer Chemotherapy. Survey Of Ophthalmology. Jan.-Feb. 2006, vol. 51, No. 1, pp. 19-40.*
Kuwano et al, "Cyclosporine A Formulation Affects Its Ocular Distribution in Rabbits", Pharmaceutical Research, vol. 19, No. 1, Jan. 2002, 108-111.

(Continued)

*Primary Examiner*—Jeffrey E Russel
(74) *Attorney, Agent, or Firm*—Joel B. German; Debra D. Condino; Allergan, Inc.

(57) ABSTRACT

Presently described are methods of administration and associated treatment of one or more ocular conditions using cyclosporine, or an analog or derivative thereof. The ocular conditions can be a result of treatment using other therapeutic agents, such as chemotherapy agents, antiviral agents and immunomodulators.

11 Claims, No Drawings

U.S. PATENT DOCUMENTS

| | | |
|---|---|---|
| 6,638,522 B1 | 10/2003 | Mulye |
| 6,656,504 B1 | 12/2003 | Bosch et al. |
| 6,720,001 B2 | 4/2004 | Chen et al. |
| 6,723,339 B2 | 4/2004 | Meinzer et al. |
| 6,852,718 B2 | 2/2005 | Burkamp et al. |
| 6,916,785 B2 | 7/2005 | Patel |
| 2001/0003589 A1 | 6/2001 | Neuer et al. |
| 2001/0036449 A1 | 11/2001 | Garst |
| 2001/0041671 A1* | 11/2001 | Napoli .................. 514/9 |
| 2002/0012680 A1 | 1/2002 | Patel et al. |
| 2002/0013272 A1 | 1/2002 | Cavanak et al. |
| 2002/0016290 A1 | 2/2002 | Floc'h et al. |
| 2002/0016292 A1 | 2/2002 | Richter et al. |
| 2002/0025927 A1 | 2/2002 | Olbrich et al. |
| 2002/0045601 A1 | 4/2002 | Kawashima et al. |
| 2002/0107183 A1 | 8/2002 | Petswzulat et al. |
| 2002/0119190 A1 | 8/2002 | Meinzer et al. |
| 2002/0165134 A1 | 11/2002 | Richter et al. |
| 2003/0060402 A1 | 3/2003 | Cavanak et al. |
| 2003/0108626 A1 | 6/2003 | Benita et al. |
| 2003/0133984 A1 | 7/2003 | Ambuhl et al. |
| 2003/0143250 A1 | 7/2003 | Hauer et al. |
| 2003/0147954 A1 | 8/2003 | Yang et al. |
| 2003/0166517 A1 | 9/2003 | Fricker et al. |
| 2003/0211983 A1 | 11/2003 | Petszulat et al. |
| 2003/0212090 A1 | 11/2003 | Chen et al. |
| 2003/0215496 A1 | 11/2003 | Patel et al. |
| 2004/0048789 A1 | 3/2004 | Patel |
| 2004/0092435 A1 | 5/2004 | Peyman |
| 2004/0101552 A1 | 5/2004 | Patel |
| 2004/0102366 A1 | 5/2004 | Patel |
| 2004/0106546 A1 | 6/2004 | Napoli |
| 2004/0161458 A1 | 8/2004 | Meinzer et al. |
| 2004/0167063 A1 | 8/2004 | Cavanak et al. |
| 2004/0185068 A1 | 9/2004 | Yu et al. |
| 2004/0198645 A1 | 10/2004 | Ambuhl et al. |
| 2005/0013854 A1 | 1/2005 | Mannino et al. |
| 2005/0025810 A1 | 2/2005 | Peyman |
| 2005/0048087 A1 | 3/2005 | Posanski |
| 2005/0059583 A1 | 3/2005 | Acheampong et al. |
| 2005/0118254 A1 | 6/2005 | Choi et al. |
| 2005/0129718 A1 | 6/2005 | Sherman |
| 2005/0147659 A1 | 7/2005 | Carli et al. |
| 2005/0196370 A1 | 9/2005 | Yu et al. |

OTHER PUBLICATIONS

Castillo, et al., "Influence of topical Cyclosporine A and dissolvent on corneal epithelium permeability of fluorescein," Documenta Ophthalmologica, 1995, 91, 49-55.

Restasis® Package Insert, (cyclosporine ophthalmic emulsion)0. 05%, Sterile, Preserviatve-Free, 2 page, (2004).

Uniqema, Tween™ Series. Polyoxyethylene derivatives of sorbitan esters. 2 pages, (2004).

Rita, Ritabate 40, INCI Nomenclature (formerly CTFA) . . . Polysorbate 40, 1 page, (1994).

Rita, Ritabate 60, INCI Nomenclature (formerly CTFA) . . . Polysorbate 60, 1 page.

Rita, Ritabate 20, INCI Nomenclature (formerly CTFA) . . . Polysorbate 20, 1 page, (1994).

TheMerkIndex Results-Form View, Monography No. 07664, Titles: Polysorbates, 1 page, and Polyoxyethylene, 1 page, (2006).

Sandimmue® Package Insert, (cyclosporine oral solution), RxList, The Internet Drug Index, 3 pp, (2006).

Benitez, et al., "Influence of topical Cyclosporine A and dissolvent on corenal epithelium permeability of fluororescein," Ophthalmologica 91: 49-55, 1995.

http://thornleycompany.com/Products/PEGsters.htm, (2006).

www.lipochemicals.com document on Emulsifiers and Emulsifying systems (Aug. 20, 2002), pp. 1-5.

Lanzetta et al, "Major ocular complications after organ transplantation", Transplantation Proceedings, vol. 36, No. 10, Dec. 1, 2004.

* cited by examiner

PREVENTION AND TREATMENT OF OCULAR SIDE EFFECTS WITH A CYCLOSPORIN

CROSS-REFERENCE TO RELATED APPLICATIONS

This application claims priority to: U.S. Provisional Patent Application No. 60/596,709, filed Oct. 14, 2005; U.S. Provisional Patent Application No. 60/597,431, filed on Nov. 30, 2005; and U.S. Provisional Patent Application No. 60/805,577, filed on Jun. 22, 2006; all of which are expressly incorporated by reference herein.

DESCRIPTION OF THE INVENTION

Patients undergoing treatment with certain therapeutically active agents can have certain ocular conditions as a result of that treatment. In particular, patients undergoing chemotherapy with a therapeutically active agent effective for treatment of a cancer often have ocular conditions as a result of that treatment.

One embodiment is a method comprising administering a cyclosporin, an analog or derivative thereof, or a combination thereof, to an eye of a mammal in combination with administration of a therapeutically active agent to said mammal, said therapeutically active agent being an chemotherapy agent or an antiviral agent, wherein said method is effective in preventing or treating an ocular condition associated with the use of said therapeutically active agent.

"Administration of a therapeutically active agent to said mammal" means administration of the therapeutically active agent to the mammal in any way that a therapeutically active agent may be administered. Thus, administration of the therapeutically active agent is not limited to the eye, but may include systemic administration via oral, intravenous, rectal, or other means; or administration locally to any part of the body by injection, implantation, topical administration, or other means.

Administration of the therapeutically active agent need not exactly overlap in time with the administration of the cyclosporin, an analog or derivative thereof, or a combination thereof. For example, the cyclosporin, analog or derivative thereof, or a combination thereof might be administered to a mammal before the mammal receives any of the therapeutically active agent to avoid the onset of the ocular condition. In another example, the cyclosporin, analog or derivative thereof, or a combination thereof, might be administered after the mammal has begun to receive the therapeutically active agent. In another example, the cyclosporin, analog or derivative thereof, or a combination thereof, might be administered after the mammal has ceased receiving the therapeutically active agent. Administration of the cyclosporin, analog or derivative thereof, or a combination thereof might also be simultaneous with the administration of the therapeutically active agent. Thus, any time relationship may exist between the mammal receiving the therapeutically active agent and the cyclosporin, analog or derivative thereof, or a combination thereof, provided that the use of the latter is reasonably related to treatment or prophylaxis of a condition associated with the former.

It may be convenient to provide a single pharmaceutical composition which comprises both (i) the cyclosporin, analog or derivative thereof, or a combination thereof and (ii) the therapeutically active agent when the agents are to be administered simultaneously. It may be convenient to provide (i) the cyclosporin, analog or derivative thereof, or a combination thereof and (ii) the therapeutically active agent in form of a kit. For example, the agents may be packaged together. For example, (i) the cyclosporin, analog or derivative thereof, or a combination thereof and (ii) the therapeutically active agent may each be packaged in conventional pharmaceutical packaging such as boxes, jars, blister packs, vials, bottles, syringes etc., and the individually packaged components may then be combined to form a kit e.g. by the use of further packaging such as a box, or by joining up the individual packages. When in kit form, the agents can be taken independently of one another, thus allowing the user freedom to decide the temporal relationship between his use of each of the agents.

Use of a cyclosporin, or an analog or derivative thereof, including cyclosporin A, for the treatment of ocular conditions occurring in a person undergoing treatment with a therapeutically active agent for the treatment of cancer is contemplated. Accordingly, a particular patient group which may benefit from the present invention is that of persons having ocular conditions resulting from the use of a chemotherapy agent.

Also contemplated is use of a cyclosporin, or an analog or derivative thereof, including cyclosporin A, for the treatment of ocular conditions occurring in a person who is undergoing treatment with an antiviral agent. Accordingly, a particular patient group which may benefit from the present invention is that of persons having ocular conditions resulting from the use of an antiviral agent.

Also contemplated is use of a cyclosporin, or an analog or derivative thereof, including cyclosporin A, for the treatment of ocular conditions occurring in a person who is undergoing treatment with an immunomodulator. Accordingly, a particular patient group which may benefit from the present invention is that of persons having ocular conditions resulting from the use of an immunomodulator.

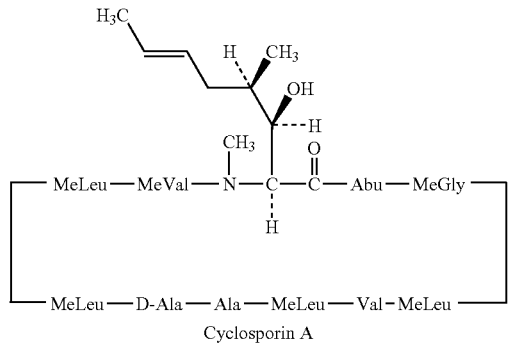

Cyclosporin A

Cyclosporin A is a cyclic peptide with immunosuppressive properties having the structure shown above. It is also known by other names including cyclosporine, cyclosporine A, ciclosporin, and ciclosporin A.

Other cyclosporins include cyclosporine b, cyclosporine D, cyclosporine G, which are well known in the art. Cyclosporin derivatives and analogs are also known in the art. For example, U.S. Pat. Nos. 6,254,860 and 6,350,442, incorporated by reference herein, illustrate several examples.

The ocular conditions to be prevented or treated are well known in the art. In particular, nasolacrimal stenosis, chemotherapy induced ocular toxicity, lacrimal duct stenosis, punctal stenosis, lacrimation, abnormal lacrimation, increased tearing, nasolacrimal blockage, keratitis, keratoconjunctivitis, conjunctivitis, or a combination thereof may be prevented or treated.

Also contemplated is a method comprising administering cyclosporin A topically to the eye of a person, wherein docetaxel is also administered to said person, wherein said method is effective in preventing or treating an ocular condition associated with the administration of docetaxel.

Although the ocular condition may be associated with any antiviral agent, the following antiviral agents are contemplated in particular:

Zalcitabine, and

Rimantadine Hydrochloride.

Although the ocular condition may be associated with any chemotherapy agent, the following chemotherapy agents are contemplated in particular:

Paclitaxel and derivatives thereof, such as Docetaxel

Doxorubicin Hydrochloride,

Irinotecan Hydrochloride,

Fluorouracil,

Imatinib Mesylate, and

Rituximab

Derivatives of paclitaxel generally include the macrocycle shown below, where derivatives are formed at a hydroxyl moiety.

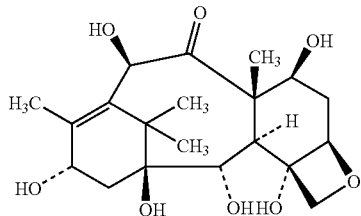

Chemotherapeutic compounds incorporating this structure are thus contemplated. For example, the structures of paclitaxel and docetaxel are shown below.

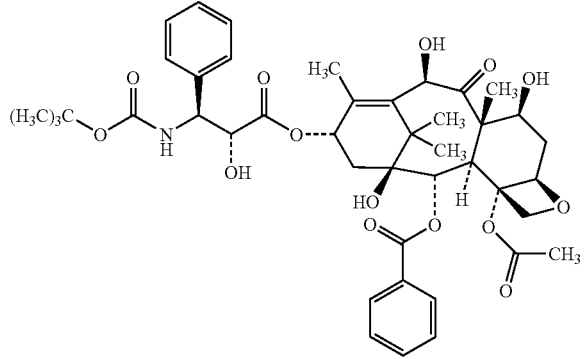
Docetaxel

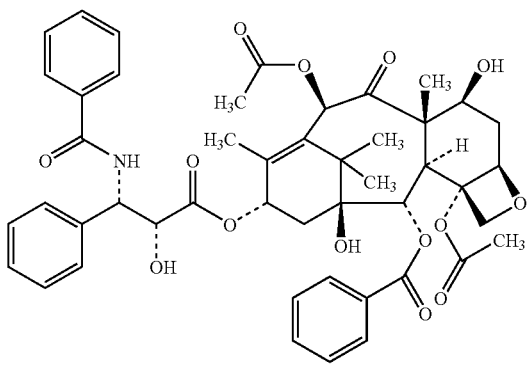
Paclitaxel

In one embodiment, the chemotherapy agent is docetaxel.

Although the ocular condition may be associated with any immunomodulator, the following immunomodulator are contemplated in particular:

Interferon alfa-2b, Recombinant

Mycophenolate Mofetil, and

Mycophenolate Mofetil Hydrochloride.

While not intending to limit the scope of the invention in any way, the following therapeutically active agents may cause lacrimal duct stenosis: docetaxel.

While not intending to limit the scope of the invention in any way, the following therapeutically active agents may cause lacrimation:

interferon alfa-2b, recombinant, doxorubicin hydrochloride, irinotecan hydrochloride, fluorouracil, docetaxel, and zalcitabine.

While not intending to limit the scope of the invention in any way, the following therapeutically active agents may cause abnormal lacrimation:

mycophenolate motefil, mycophenolate motefil hydrochloride, imatinib mesylate, ritumixab, and rimantadine hydrochloride.

While not intending to limit the scope of the invention in any way, the following therapeutically active agents may cause keratitis:

Amantadine Hydrochloride,

Erlotinib,

Bexarotene, and

Voriconazole.

While not intending to limit the scope of the invention in any way, the following therapeutically active agents may cause keratoconjunctivitis:
Capecitabine.

While not intending to limit the scope of the invention in any way, the following therapeutically active agents may cause conjunctivitis:

Risedronate Sodium,

Leflunomide,

Mycophenolate Mofetil,

Oxaliplatin,

Cetuximab,

Ribavirin,

Rituximab,

Basiliximab,

Erlotinib,

Capecitabine,

Doxorubicin Hydrochloride,

Imiquimod,

Amphotericin B, liposomal,

Zolpidem Tartrate,

Glatiramer Acetate,

Epirubicin Hydrochloride,

Saquinavir,

Enfuvirtide,

Imatinib Mesylate,

Gefitinib,

Lamotrigine,

Delavirdine Mesylate,

Rituximab,

Ivermectin,

Palivizumab,

Oseltamivir Phosphate,

Bexarotene,

Docetaxel,

Abacavir Sulfate,

Lamivudine,

Zidovudine,

Voriconazole,

Nevirapine,

Ribavirin, and

Abacavir Sulfate.

Additionally, one or more of the ocular conditions disclosed herein may be associated with the following therapeutically active agents: abacavir sulfate, amantadine hydrochloride, amphotericin B, basiliximab, bexarotene, capecitabine, cetuximab, delavirdine mesylate, docetaxel, doxorubicin hydrochloride, enfuvirtide, epirubicin hydrochloride, erlotinib, fluorouracil, gefitinib, glatiramer acetate, imatinib mesylate, imiquimod, interferon alfa-2b, irinotecan hydrochloride, ivermectin, lamivudine, lamotrigine, leflunomide, mycophenolate mofetil, mycophenolate mofetil hydrochloride, nevirapine, oseltamivir phosphate, oxaliplatin, palivizumab, ribavirin, rimantadine hydrochloride, risedronate sodium, rituximab, saquinavir, voriconazole, zalcitabine, zidovudine, and zolpidem tartrate.

The therapeutically active agent is administered in the usual manner known in the art for the condition being treated.

Alternatively, a therapeutically active agent and cyclosporin A may be administered in a single composition.

Useful compositions are disclosed in the following patent applications, each of which is expressly incorporated by reference herein: U.S. patent application Ser. No. 11/181,409, filed on Jul. 13, 2005; U.S. patent application Ser. No. 11/181,509, filed on Jul. 13, 2005; U.S. patent application Ser. No. 11/181,187, filed on Jul. 13, 2005; U.S. patent application Ser. No. 11/181,178, filed on Jul. 13, 2005; U.S. patent application Ser. No. 11/181,428, filed on Jul. 13, 2005; U.S. patent application Ser. No. 11/255,821, filed on Oct. 19, 2005; U.S. patent application Ser. No. 11/161,218, filed on Jul. 27, 2005; and U.S. Provisional Patent Application Ser. No. 60/727,684, filed on Oct. 17, 2005.

In one embodiment, cyclosporin A is administered in the form of Restasis®, available from Allergan, Inc. The cyclosporin A is administered twice a day as indicated on the package insert.

Although there has been hereinabove described pharmaceutical compositions for the purpose of illustrating the manner in which the invention may be used to advantage, it should be appreciated that the invention is not limited thereto. Accordingly, any and all modifications, variations, or equivalent arrangements, which may occur to those skilled in the art, should be considered to be within the scope of the present invention as defined in the appended claims.

What is claimed is:

1. A method comprising administering cyclosporin A to an eye of a mammal in combination with administration of docetaxel to said mammal, wherein said method is effective in treating keratoconjunctivitis or conjunctivitis.

2. A method comprising administering cyclosporin A to an eye of a mammal in combination with administration of docetaxel or fluorouracil to the mammal, wherein the method is effective to treat abnormal lacrimation, keratitis, keratoconjunctivitis, or conjunctivitis.

3. The method of claim 2, wherein the method is effective to treat abnormal lacrimation.

4. The method of claim 2, wherein the method is effective to treat keratitis.

5. The method of claim 2, wherein the method is effective to treat keratoconjunctivitis.

6. The method of claim 2, wherein the method is effective to treat conjunctivitis.

7. A method comprising the step of administering cyclosporin A to an eye of a mammal undergoing treatment with docetaxel or fluorouracil, wherein the method is effective to treat abnormal lacrimation, keratitis, keratoconjunctivitis, or conjunctivitis.

8. The method of claim 7, wherein the method is effective to treat abnormal lacrimation.

9. The method of claim 7, wherein the method is effective to treat keratitis.

10. The method of claim 7, wherein the method is effective to treat keratoconjunctivitis.

11. The method of claim 7, wherein the method is effective to treat conjunctivitis.

* * * * *